United States Patent [19]

Rao

[11] Patent Number: 5,545,774
[45] Date of Patent: Aug. 13, 1996

[54] PROCESS FOR THE MANUFACTURE OF 1,1,1,3,3,3-HEXAFLUOROPROPANE

[75] Inventor: V. N. Mallikarjuna Rao, Wilmington, Del.

[73] Assignee: E. I. Du Pont de Nemours and Company, Wilmington, Del.

[21] Appl. No.: 352,004

[22] Filed: Dec. 8, 1994

[51] Int. Cl.$^6$ .................................................. C07C 17/08
[52] U.S. Cl. ........................................... 570/168; 570/169
[58] Field of Search ..................................... 570/168, 169

[56] References Cited

U.S. PATENT DOCUMENTS

| | | | |
|---|---|---|---|
| 3,632,834 | 1/1972 | Christoph, Jr. | 260/653.7 |
| 3,859,424 | 1/1975 | Scherer et al. | 423/472 |
| 5,171,901 | 12/1992 | Gassen et al. | 570/168 |
| 5,414,165 | 5/1995 | Nappa et al. | 570/169 |

FOREIGN PATENT DOCUMENTS

| | | |
|---|---|---|
| 2073533 | 1/1993 | Canada . |
| 0522639 | 1/1993 | European Pat. Off. . |
| 468447 | 7/1937 | United Kingdom . |
| WO95/12563 | 5/1995 | WIPO . |

OTHER PUBLICATIONS

M. Belbachir, et al., "Telomerisation Du Chlorure De Vinylidene, 1 Reaction Avec Le Tetrachlorure De Carbone Par Catalyse Redox", *Makromol. Chem.*, 185, 1583–1595 (1984).

*Primary Examiner*—Alan Siegel

[57] ABSTRACT

A process is disclosed for producing 1,1,1,3,3,3-hexafluoropropane. The process involves contacting 1,1,1,3,3,3-hexachloropropane with hydrogen fluoride in the vapor phase at a temperature of from about 250° C. to 400° C. in the presence of a catalyst of trivalent chromium supported on carbon. The carbon has an ash content sufficiently low to produce $CF_3CH_2CF_3$ with a selectivity of at least about 70 percent based upon the amount of 1,1,1,3,3,3-hexachloropropane reacted with HF.

10 Claims, No Drawings

PROCESS FOR THE MANUFACTURE OF 1,1,1,3,3,3-HEXAFLUOROPROPANE

FIELD OF THE INVENTION

This invention relates to processes for the manufacture of 1,1,1,3,3,3-hexafluoropropane (i.e., $CF_3CH_2CF_3$ or HFC-236fa) by the reaction of 1,1,1,3,3,3-hexachloropropane (i.e., $CCl_3CH_2CCl_3$ or HCC-230fa) with hydrogen fluoride.

BACKGROUND

HFC-236fa is useful as a refrigerant, fire extinguishant, heat transfer medium, gaseous dielectric, sterilant carrier, polymerization medium, particulate removal fluid, carrier fluid, buffing abrasive agent, displacement drying agent and power cycle working fluid. In particular, HFC-236fa is a highly effective refrigerant. Canadian Patent No. 2,073,533 discloses a liquid phase process for the manufacture of 1-chloro-1,1,3,3,3-pentafluoropropane (i.e., $CClF_2CH_2CF_3$ or HCFC-235fa) and HFC-236fa by contacting HCC-230fa with HF in the presence of a liquid phase catalyst (e.g., tin and antimony compounds). An example illustrates conversion of all of the 1,1,1,3,3,3-hexachloropropane, with an overall selectivity to HCFC-235fa and HFC-236fa higher than 45 mole % with respect to the HFC-230fa converted.

HFC-236fa has been prepared by vapor phase chlorine substitution processes in which the yields have typically been less than about 70%. For example, U.S. Pat. No. 5,171,901 discloses inter alia a process for the preparation of HFC-236fa (and 2-chloro-1,1,1,3,3,3-hexafluoropropane) by contacting a mixture of hexachloropropene and HF with a catalyst (e.g., chromium III salts). The catalyst can be used as such or deposited on a support, for example on alumina, magnesium oxide, magnesium fluoride, calcium fluoride, zinc chloride and/or activated carbon. Exemplified reactions using a mixture of $CrCl_3$ and $MgF_2$ at temperatures ranging from 350° C. to 500° C. provided yields of HFC-236fa as follows: 350° C., none detected; 400° C., 10%; 450° C., 55%; and 500° C., 64%. Other products formed in varying amounts were $CF_3CHClCF_3$, $CF_3CCl_2CF_3$, $CF_3CCl=CF_2$, $CF_3CCl=CClF$, and $CF_3CCl=CCl_2$. U.S. Pat. No. 3,859,424 discloses (Example 10) a process for the reaction of 1,1,1,3-tetrachloropropane and HF over a fluorinated chromic hydroxide catalyst at 200° C. The major product (58%) obtained was 1,1,1-trifluoropropene; and the other product identified (28.5%) was 1,1,1-trifluoro-3-chloropropane.

There is an interest in developing more efficient vapor phase processes for the manufacture of HFC-236fa.

SUMMARY OF THE INVENTION

A process is provided in accordance with this invention for producing 1,1,1,3,3,3-hexafluoropropane. The process comprises contacting 1,1,1,3,3,3-hexachloropropane with hydrogen fluoride in the vapor phase at a temperature of from about 250° C. to 400° C. in the presence of a catalyst of trivalent chromium supported on carbon, said carbon having an ash content (preferably less than about 0.5 percent by weight) sufficiently low to produce $CF_3CH_2CF_3$ with a selectivity of at least about 70 percent based upon the amount of 1,1,1,3,3,3-hexachloropropane reacted with HF.

DETAILED DESCRIPTION

The present invention provides a process for the manufacture of 1,1,1,3,3,3-hexafluoropropane (i.e., $CF_3CH_2CF_3$ or HFC-236fa) by contacting a mixture of hydrogen fluoride and 1,1,1,3,3,3-hexachloropropane (i.e., $CCl_3CH_2CCl_3$ or HCC-230fa) in the vapor phase in the presence of catalyst where trivalent chromium is supported on low-ash carbon. Of note are catalysts where the trivalent chromium is in the form of a chromium halide. Typically the catalyst consists essentially of trivalent chromium (e.g., $CrCl_3$ and/or $CrF_3$) supported on a carbon which has an ash content of less than about 0.5 weight percent. More preferably, the ash content of the carbon is less than about 0.3 weight percent. Supported trivalent chromium catalysts suitable for use in the process of this invention can be prepared in a manner similar to that disclosed in U.S. Pat. No. 3,632,834, provided the carbon used has a sufficiently low ash content. Preferred catalysts include a low-ash content carbon support (as described herein) containing chromium chloride ($CrCl_3$), fluorided chromium chloride (e.g., $CrCl_3$ treated with HF to produce chromium chlorofluoride (s)), or mixtures of chromium chloride and chromium fluoride ($CrF_3$). While such low-ash carbon supports may be obtained using a variety of methods, a preferred carbon support is acid-washed activated carbon prior to impregnating it with trivalent chromium. Preferably the chromium content (expressed as $CrCl_3$) is from about 5 to 60 weight percent of the carbon support.

An initial acid treatment typically uses an acid other than hydrofluoric acid. Preferred acids used for the acid treatment contain neither phosphorus nor sulfur. Examples of acids which may be used in the first acid wash during the catalyst preparation process include organic acids such as acetic acid and inorganic acids such as hydrochloric acid or nitric acid. Preferably, hydrochloric acid or nitric acid is used. The second acid treatment, when employed, advantageously uses hydrofluoric acid. Normally, the carbon is treated with acid such that after such treatment the carbon contains less than about 0.5% by weight ash. Preferably, the carbon also contains less than about 200 ppm phosphorus and less than about 200 ppm sulfur; more preferably less than 100 ppm phosphorus and less than 100 ppm sulfur; and most preferably less than 50 ppm phosphorus and less than 50 ppm sulfur. The preferred carbons of this invention also contain less than about 200 ppm potassium. Washing the carbon with an acid which provides removal of excess potassium as well as phosphorus and sulfur is thus particularly preferred. Most preferably the carbon supports of this invention contain less than about 100 ppm sodium and/or less than about 100 ppm iron. Accordingly, washing with acids that remove excess sodium and iron is especially preferred.

Commercially available carbons which may be treated with acids to provide suitable supports include those sold under the following trademarks: Darco™, Nuchar™, Columbia SBV™, Columbia MBV™, Columbia MBQ™, Columbia JXC™, Columbia CXC™, Calgon PCB™, Norit™ and Barnaby Cheny NB™. The carbon support can be in the form of powder, granules, or pellets, etc.

The acid treatment may be accomplished in several ways. A suitable procedure is as follows. A carbon support is soaked overnight with gentle stirring in a 1 molar solution of the acid prepared in deionized water. The carbon support is then separated and washed with deionized water until the pH of the washings is about 3. Preferably, the carbon support is then soaked again with gentle stirring in a 1 molar solution of the acid prepared in deionized water for 12 to 24 hours. The carbon support is then finally washed with deionized water until the washings are substantially free of the anion of the acid (e.g., $Cl^-$ or $NO_3^-$), when tested by standard procedures. The carbon support is then separated and dried at about 120° C. The washed carbon is then soaked, if necessary, in 1 molar HF prepared in deionized water for about 48 hours at room temperature with occasional stirring. The carbon support is separated and washed repeatedly with deionized water until the pH of the washings is greater than 4. The carbon support is then dried followed by calcination at 300° C. for about 3 hours in air prior to its use as a support. Reference is made to U.S. Pat. No. 5,136,113 for further details relating to producing acid-washed carbon catalysts. Of note is a catalyst prepared by acid washing a carbon to provide a low-ash carbon (e.g., a carbon having an ash content of less than about 0.5 percent by weight), impregnating said low-ash carbon with an aqueous solution of chromium chloride, drying the impregnated carbon, and activating the dried impregnated carbon with gaseous HF at elevated temperature.

The starting material, HCC-230fa, can be prepared by the reaction of carbon tetrachloride with vinylidene chloride as disclosed in Belbachir et al. Makromol. Chem., Vol. 185, pp. 1583–1595 (1984) (see Chemical Abstracts 101: 131167).

Typically, both $CF_3CH_2CF_3$ and haloprecursors of $CF_3CH_2CF_3$ are produced by catalyst contact. The catalysts of the present invention are used to provide highly selective production of HFC-236fa and its halo precursors. By halo precursors of $CF_3CH_2CF_3$ is meant saturated compounds of the formula $CX_3CH_2CX_2Cl$ and olefinic compounds of the formula $CX_2=CHCX_3$ where each X is Cl or F and at least one X in the halo precursor compound is F. These halo precursors may be recycled to the reaction for further reaction with HF in the presence of trivalent chromium on carbon with an ash content of less than about 0.5% by weight to produce additional HFC-236fa such that the overall selectivity to 236fa from 230fa is high. Preferably, the total selectivity to $CF_3CH_2CF_3$ and its haloprecursors is at least about 95 percent and a sufficient amount of said haloprecursors is reacted with hydrogen fluoride in the vapor phase at a temperature of from about 250° C. to 400° C. in the presence of said catalyst to provide an overall selectivity to 1,1,1,3,3,3-hexafluoropropane of at least about 90 percent. Of note are embodiments where the process is run to produce HFC-236fa itself with a selectivity of at least about 95 percent prior to separation of the HFC-236fa from the halo precursors or other reaction by-products. This may be achieved for example by providing sufficient catalyst contact time in a single pass reaction system to allow substantially complete replacement of chlorine by fluorine and saturation of any olefinic halo precursors. Alternatively, the reactor effluent can be recycled (optionally with additional HF) for further catalyst contact.

Preferred catalysts (especially where selectivity to HFC-236fa of about 90 percent or more is desired prior to separation of the HFC-236fa from the halo precursors or other reaction by-products) include trivalent chromium on carbon with an ash content of less than about 0.5% by weight, containing at least 5% by weight chromium based on the support (expressed as $CrCl_3$) which are pretreated with a vaporizable fluorine-containing compound (e.g., HF or $CCl_3F$). These pretreated catalysts are most preferred, and are suitable for obtaining at least about 90% selectivity to HFC-236fa itself prior to separation of the HFC-236fa from its halo precursors or other reaction by-products (e.g., in a single pass over the catalyst).

The molar ratio of HF to $CCl_3CH_2CCl_3$ is typically within the range of from about 1:1 to about 100:1, and is preferably within the range of about 6:1 to about 20:1. $HF:CCl_3CH_2CCl_3$ ratios lower than about 6 result in incomplete conversion of the 1,1,1,3,3,3-hexachloropropane starting material. $HF:CCl_3CH_2CCl_3$ ratios greater than about 20 have little advantage and result in large amounts of HF being recycled or discarded.

The process of the present invention is suitably conducted at a temperature in the range of from about 250° C. to 400° C., preferably from about 250° C. to about 350° C., and more preferably, from about 250° C. to 325° C. Temperatures below about 200° C. result in low conversion of the 1,1,1,3,3,3-hexachloropropane starting material. The contact time of reactants with the catalyst bed is typically from about 0.2 second to about 60 seconds.

The pressure is not critical but should be sufficient to maintain HF, 1,1,1,3,3,3-hexachloropropane and the reaction product stream components in the vapor state at the operating temperature.

In general, the higher the temperature, the greater the HF reactant mole ratio, and the longer the contact time, the greater is the conversion of 1,1,1,3,3,3-hexachloropropane.

The reaction products may be separated by conventional techniques such as distillation. 1,1,1,3,3,3-Hexafluoropropane and HF form an azeotrope which can be recovered from the reaction products by using conventional techniques such as decantation and distillation. Reaction products such as $CF_3CH=CCl_2$, $CCl_2FCH=CF_2$, or $CF_3CH_2CClF_2$ which are halo precursors of HFC-236fa can be separated from the reaction products and advantageously returned to the reactor for conversion to $CF_3CH_2CF_3$.

The process of this invention can be carried out readily in the vapor phase using well known chemical engineering practice.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel.

Practice of the invention will become further apparent from the following non-limiting examples.

EXAMPLES

Activation Procedure

A ⅝" (1.58 cm) I.D. Inconel® nickel alloy reactor was charged with a catalyst and heated to 300° C. in a flow of nitrogen (25 mL/min) for about 2 hours. The temperature was reduced to 175° C. and a 2:1 molar ratio of nitrogen and HF was started through the reactor (total flow 100 mL/min). After one hour under these conditions, the molar ratio of nitrogen to HF was adjusted to 1:3 and the temperature increased gradually over a two hour period to 400° C. The reactor was then brought back to the desired operating temperature, the nitrogen flow stopped, and the flow of reactants started.

Carbon Support

The carbon support used in the example was a 4×8 mesh (about 4.7 mm×2.4 mm) commercial grade coconut shell carbon which had (before washing) an ash content of about 2.6 weight percent. After hydrochloric acid washing, the carbon support had an ash content of less than about 0.1 weight percent.

Preparation of 20% $CrCl_3$ on Acid-Washed Carbon

Acid-washed carbon (100 g), prepared as described above, was added to a solution of $CrCl_3.6H_2O$ (33.65 g) dissolved in deionized water (400 mL). The slurry was maintained at room temperature for about 2 hours with occasional stirring. Water was then removed using a rotary evaporator. The granules were then dried at 130° C. in a nitrogen atmosphere for 18 hours to provide 116.1 g of 20% $CrCl_3$ on acid-washed carbon.

Analytical Procedure

The reactor effluent was sampled on-line with a Hewlett Packard HP 5890 gas chromatograph using a 20 foot (6.1 m) long, one-eighth inch (0.32 cm) diameter, column containing Krytox™ perfluorinated polyether on an inert support and a helium flow of 35 mL/min. Gas chromatographic conditions were 70° C. for three minutes followed by temperature programming to 180° C. at a rate of 6° C./minute. The table percentages are in mole %.

EXAMPLE

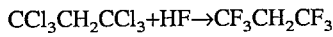
$CCl_3CH_2CCl_3 + HF \rightarrow CF_3CH_2CF_3$

The reactor was charged with a 20% $CrCl_3$ on acid-washed carbon (30 mL, 13.3 g) catalyst and the catalyst was activated according to the Activation Procedure above. The reaction temperature was varied from 325 to 250° C., the molar ratio of HF to $CCl_3CH_2CCl_3$ (HCC-230fa) was 8:1, and the contact time was 30 seconds. The reaction effluent was analyzed according to the Analytical Procedure above. The reaction results are shown in Table 1.

TABLE 1

| Temp. | 236fa[1] | 1224[2] | 226da[3] | 235fa[4] | 1214xc[5] | 1223[6] | 1213xa[7] | Others[8] |
|---|---|---|---|---|---|---|---|---|
| 325 | 90.5 | 0.9 | 1.8 | 0.4 | 0.7 | 1.9 | 2.3 | 1.5 |
| 300 | 93.0 | 0.7 | 0.5 | 0.6 | 0.5 | 2.3 | 1.4 | 1.0 |
| 275 | 91.1 | 0.7 | 0.2 | 1.0 | 0.4 | 4.0 | 0.1 | 1.3 |
| 250 | 74.1 | 2.3 | 0.1 | 6.6 | 0.4 | 14.0 | 1.1 | 1.5 |

[1]236fa is $CF_3CH_2CF_3$
[2]1224 is a mixture of $C_3HClF_4$ isomers
[3]226da is $CF_3CHClCF_3$
[4]235fa is $CClF_2CH_2CF_3$
[5]1214xc is $CF_2=CClCF_3$
[6]1223 is $CCl_2=CHCF_3$
[7]1213xa is $CCl_2=CClCF_3$
[8]Others include $CF_2=CHCF_3$, $C_4H_6F_4$, and/or $CF_3CCl_2CF_3$

COMPARATIVE EXAMPLE

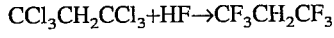
$CCl_3CH_2CCl_3 + HF \rightarrow CF_3CH_2CF_3$

The reactor was charged with a commercially available 30% $CrCl_3$ on carbon catalyst and the catalyst (30 mL, 13.3 g) was activated according to the Activation Procedure above. The reaction temperature was 325° C., the molar ratio of HF to $CCl_3CH_2CCl_3$ (HCC-230fa) was 8:1, and the contact time was 30 seconds. The reaction effluent was analyzed according to the Analytical Procedure above. The reaction results are shown in Table A.

TABLE A

| TOS[1] | 1225zc[2] | 236fa | 1224 | 226da | 235fa | 1214xc | 1223 | 1213xa | Others[3] |
|---|---|---|---|---|---|---|---|---|---|
| 0.5 | 0.4 | 87.6 | 0.2 | 3.3 | 0.2 | 0.7 | 0.3 | 2.4 | 3.5 |
| 2.0 | 0.9 | 78.9 | 2.2 | 1.0 | 0.8 | 1.8 | 7.7 | 5.7 | 0.9 |
| 6.0 | 5.0 | 46.8 | 9.4 | 0.2 | 2.9 | 0.8 | 31.9 | 2.2 | 0.8 |

[1]TOS is time on stream in hours
[2]1225zc is $CF_2=CHCF_3$
[3]Others include $C_4H_6F_4$ and $CF_3CCl_2CF_3$ In contrast, the yield of 236fa using the low-ash content example catalyst at 325° C. averaged 89.0% over 26 hours on stream; at 300° C. averaged 93.3% over 31 hours on stream; and at 275° C. averaged 92.1% over 39 hours on stream.

What is claimed is:

1. A process for producing 1,1,1,3,3,3-hexafluoropropane, comprising
    contacting 1,1,1,3,3,3-hexachloropropane with hydrogen fluoride in the vapor phase at a temperature of from about 250° C. to 400° C. in the presence of a catalyst of trivalent chromium supported on carbon, said carbon having an ash content sufficiently low to produce $CF_3CH_2CF_3$ with a selectivity of at least about 70 percent based upon the amount of 1,1,1,3,3,3-hexachloropropane reacted with HF.

2. The process of claim 1 wherein the ash content of the carbon is less than about 0.5 percent by weight.

3. The process of claim 1 wherein the catalyst consists essentially of trivalent chromium supported on carbon which has an ash content of less than about 0.5 weight percent.

4. The process of claim 1 wherein the carbon contains less than about 200 ppm phosphorus and less than 200 ppm sulfur.

5. The process of claim 1 wherein the molar ratio of HF to $CCl_3CH_2CCl_3$ is within the range of from about 1:1 to about 20:1.

6. The process of claim 1 wherein both $CF_3CH_2CF_3$ and haloprecursors of $CF_3CH_2CF_3$ are produced by catalyst contact; wherein the total selectivity to $CF_3CH_2CF_3$ and its haloprecursors is at least about 95 percent; and wherein a sufficient amount of said haloprecursors is reacted with hydrogen fluoride in the vapor phase at a temperature of from about 250° C. to 400° C. in the presence of said catalyst to provide an overall selectivity to 1,1,1,3,3,3-hexafluoropropane of at least about 90 percent.

7. The process of claim 1 wherein the trivalent chromium is in the form a chromium halide.

8. The process of claim 7 wherein the ash content of the carbon is about 0.5 percent by weight or less.

9. The process of claim 1 wherein the catalyst is prepared by acid washing a carbon to provide a low-ash carbon, impregnating the low-ash carbon with an aqueous solution of chromium chloride, drying the impregnated carbon, and activating the dried impregnated carbon with gaseous HF at an elevated temperature.

10. The process of claim 9 wherein the ash content of the acid-washed carbon is less than about 0.5 percent by weight.

* * * * *